US00RE34219E

United States Patent [19]

Lederer

[11] E Patent Number: Re. 34,219

[45] Reissued Date of Patent: Apr. 13, 1993

[54] SOUND SYSTEM

[76] Inventor: Wayne A. Lederer, 1781 Bay Blvd., Atlantic Beach, N.Y. 11509

[21] Appl. No.: 591,789

[22] Filed: Oct. 2, 1990

Related U.S. Patent Documents

Reissue of:

[64] Patent No.: 4,933,981
Issued: Jun. 12, 1990
Appl. No.: 333,335
Filed: Apr. 5, 1989

[51] Int. Cl.[5] ..... H04R 1/02

[52] U.S. Cl. ..... 381/90; 381/190; 381/191; 381/205; 381/188; 381/88; 381/154

[58] Field of Search ..... 381/190, 191, 88, 89, 381/90, 188, 205, 154

[56] References Cited

U.S. PATENT DOCUMENTS

| | | | |
|---|---|---|---|
| 4,190,784 | 2/1980 | Massa | 381/190 |
| 4,458,170 | 7/1984 | Takayama et al. | 381/190 |
| 4,597,100 | 6/1986 | Grodinsky et al. | 381/99 |
| 4,701,952 | 10/1987 | Taylor | 381/25 |

*Primary Examiner*—Forester W. Isen

*Attorney, Agent, or Firm*—Ostrolenk, Faber, Gerb & Soffen

[57] ABSTRACT

A sound or acoustic system constructed entirely of magnetically inert components which remain unaffected by magnetic fields. A magnetically inert panel is provided, with at least one magnetically-inert transducer being mounted upon this panel. At least one hollow channel extends into the panel from an edge thereof, while a hole is positioned within the panel to communicate at one end with the channel and to open at an opposite end adjacent the transducer.

14 Claims, 5 Drawing Sheets

SOUND SYSTEM

Matter enclosed in heavy brackets [ ] appears in the original patent but forms no part of this reissue specification; matter printed in italics indicates the additions made by reissue.

BACKGROUND OF THE INVENTION

The present invention is directed to an acoustic system, which is especially applicable to provide sound and communication to an individual undergoing Magnetic Resonance Imaging (MRI).

Magnetic Resonance Imaging (MRI) has recently come into tremendous use, for medical diagnostic purposes. In this procedure, an MRI scanner is disposed in a room shielded from radio frequencies, such an MRI scanner being generally about 8 feet wide, and about 12 feet deep. The center bore of the MRI is about 3 feet in diameter. An individual is then passed into the MRI scanner after the same is activated, whereby the anatomical area of the individual to be diagnosed is scanned by the MRI device.

Previously, attempts have been made to provide intercom systems, and to also provide relaxing sounds such as music to an individual undergoing the MRI.

Recently, new high field MRI systems have come into use which create more noise. For example, Radiology, November 1988, page 539, describes patients experiencing hearing loss from MRI scanning.

Accordingly, there has been a long-felt need both to improve communications with a patient during the MRI scanning, and to also provide such a patient with soothing music while the MRI scanning is carried out, since the MRI device can feel quite confining.

SUMMARY OF THE INVENTION

Accordingly, it is an object of the present invention to improve MRI scanning productivity and comfort of a patient undergoing MRI scanning.

It is further object of the present invention to improve provision of sound to an individual undergoing MRI scanning and to also improve communication with the individual, when the actual scanning itself is being carried out.

It is another object of the present invention to provide a communication/public address system which remains in contact with the patient while MRI scanning is carried out.

These and other objects are attained by the present invention which is directed to a sound system constructed entirely of magnetically inert components, which remain unaffected by magnetic fields and do not affect imaging quality, the system comprising a magnetically inert panel, at least one magnetically-inert transducer mounted on the panel, at least one hollow channel extending into the panel from an edge thereof, and a hole which is positioned within the panel to communicate at one end thereof with the channel, and to open adjacent the transducer at an opposite end thereof. The components are also preferably rf-shield, while an rf-tight enclosure may be provided in which the panel is mounted. The rf-tight enclosure has an opening to allow a wave guide tube to pass therethrough and to communicate with the channel.

A pair of transducers are preferably provided, one of which is a high-frequency transducer and the other of which is a low frequency transducer, with the panel having a pair of holes, each hole being positioned to communicate with the channel at one end thereof, and to open adjacent the high frequency or low frequency transducer at an opposite end thereof.

A pair of the hollow channels is preferably provided extending into the panel, with a pair of high frequency transducers and a pair of low frequency transducers being mounted upon the panel, and two pairs of holes being positioned in the panel. A hole of each pair is positioned in the panel to communicate at one end thereof with one of the channels, and to open adjacent a respective high frequency or low frequency transducer at an opposite end thereof.

Electrically conductive, non-ferrous material tubing is preferably mounted in the opening of the rf-tight enclosure, and extends into and out of the enclosure. In the case where two openings are provided in the enclosure, a pair of such tubing is thus provided to act as a wave guide.

Furthermore, the present invention is also directed to an earpiece for an acoustic headset, which can preferably be coupled to the sound system of the present invention. This earpiece is formed of closed-cell foam, is substantially conically-shaped, and also has a passage extending therethrough from substantially an apex of the conical shape, whereby noise generated by the scanning procedure is attenuated.

The present invention provides a sound system utilizing magnetically inert components which are not affected by high flux magnetic fields. The present invention utilizes pneumatic headphones or a headset, which supply a patient with soothing music, e.g., stereo high fidelity quality music and/or serve as an intercom, while the patient is being tested by the Magnetic Resonance Imaging (MRI) scanner. The sound system of the present invention will not degrade imaging qualities of MRI, and will not increase the noise to signal ratio or create artifacts.

As noted above, the present invention can provide soothing music to a patient, and can also serve as an intercom, while the MRI test is being carried out. Prior to the present invention, the only communication to a patient that was possible, was only between a series of tests, i.e., when the MRI gradients did not make any noise. Such noise would mask a speaker.

With the present invention, even while the gradient noise is present, there can still be communication between a patient and the operator, because the headset earpiece attenuates gradient noise and introduces sound directly into the ear canals of a patient.

In previous systems utilizing pneumatic tubing, the tubing running from the transducer to the patient had to be extremely long, e.g., on the order of 25 to 30 feet in length. However, with the present invention, the tubing running from the actual transducer to the headset of a patient can be much shorter, e.g., on the order of about seven to eight feet. The previous systems clearly resulted in inferior sound quality. However, with the present invention, ambient noise from the gradients is greatly attenuated, and sound quality is greatly improved.

BRIEF DESCRIPTION OF THE DRAWINGS

The present invention will now be described in greater detail with reference ,to preferred embodiments thereof illustrated in the accompanying drawings, in which.

DESCRIPTION OF THE PREFERRED EMBODIMENTS

Figure 2:
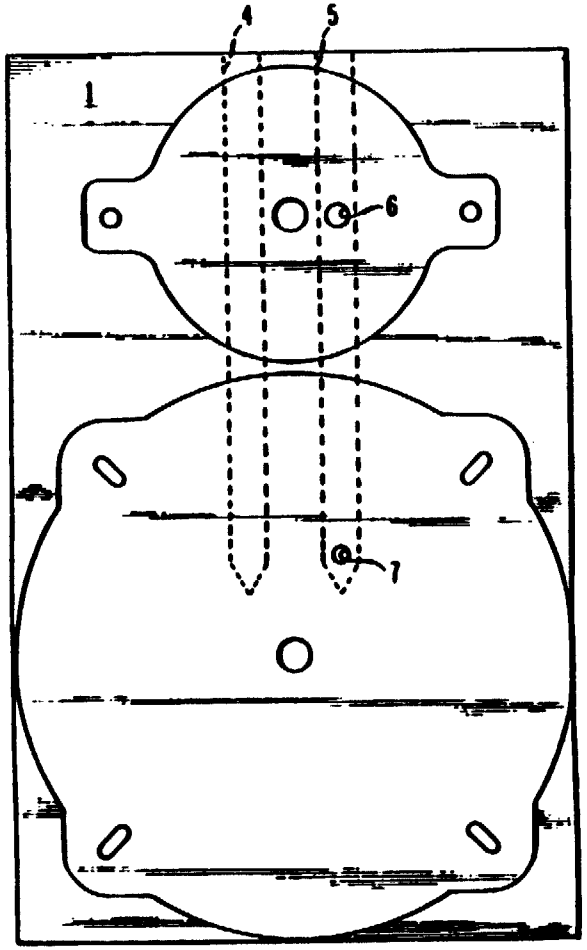
FIG. 2 is a front view similar to FIG. 1, but with the front speakers or transducers having been removed from the panel.
Figure 1:
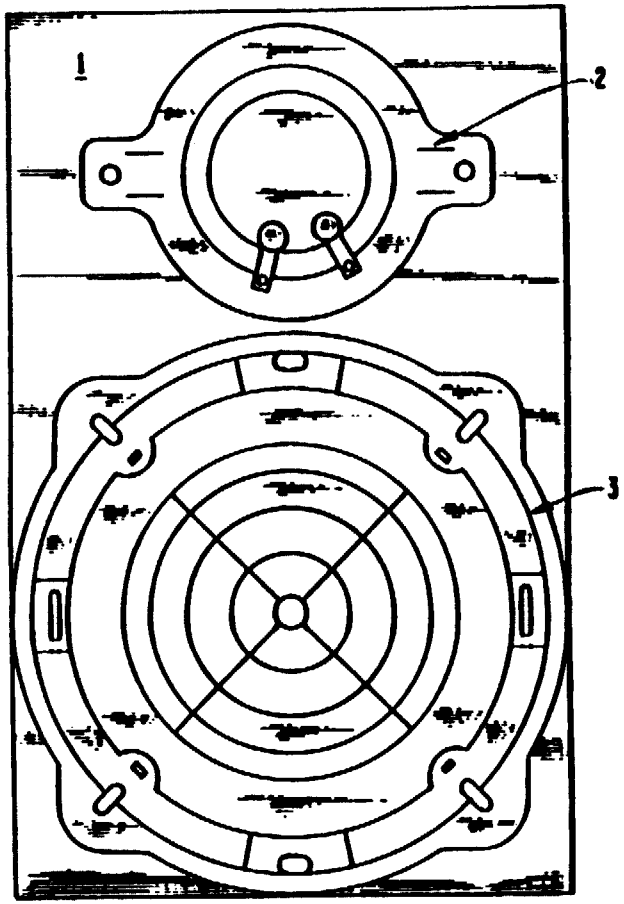
FIG. 1 is a front view of a panel in the acoustic system in accordance with the present invention.
Figure 5:
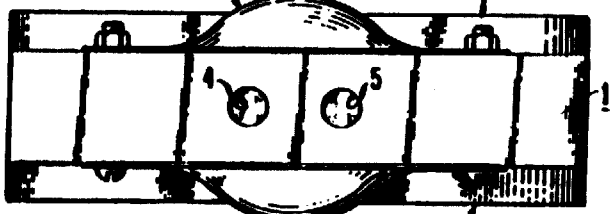
FIG. 5 is a top view of the panel of FIG. 1.
Figure 4:
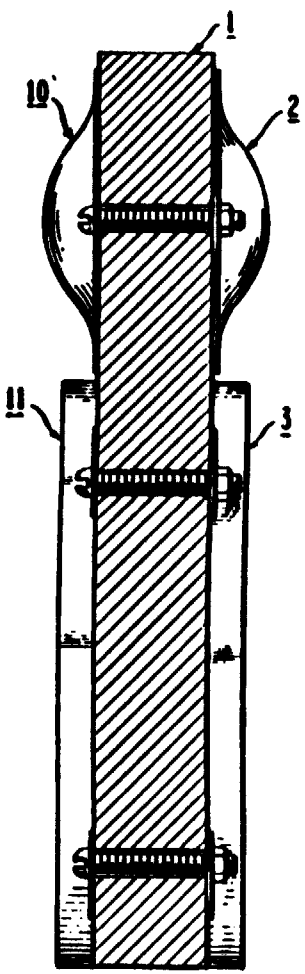
FIG. 4 is a side view of the panel of FIG. 1.
Figure 3:
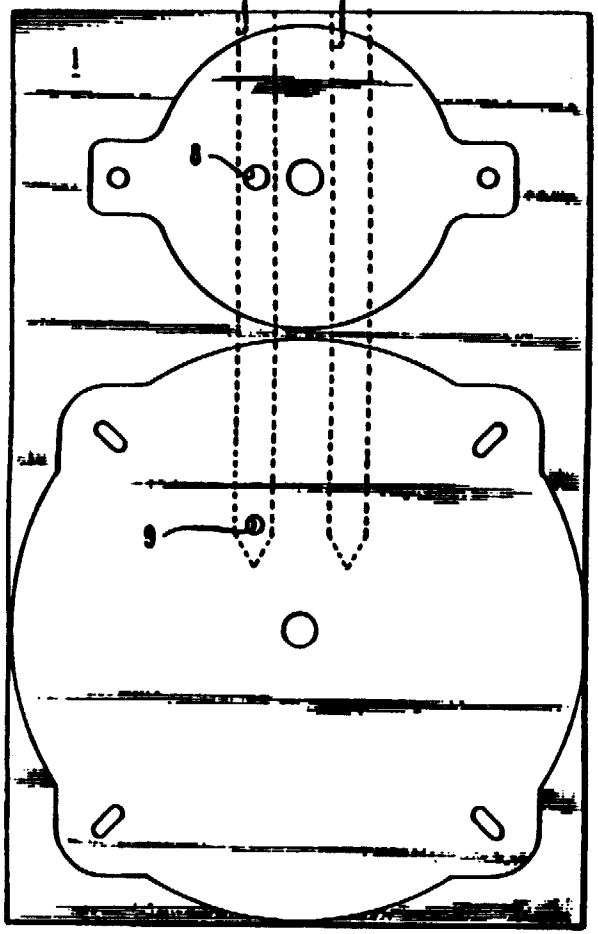
FIG. 3 is a back view of the panel of FIGS. 1 and 2, without any speaker situated thereon.

Referring to the drawings, the present invention is composed of a panel 1 formed of any non-magnetic material (N.M.M.), which functions as a mechanical catalyst for transforming ambient sound from a transducer and converting the same into a pneumatic sound pressure level. More specifically, two acoustic channels 4, 5 are bored into the panel 1 itself. The panel 1 of the present invention is suitable for mounting a pair of transducers on either side thereof, e.g., a high frequency transducer 2 and a low frequency transducer 3 on opposite sides thereof. The acoustical channels 4, 5 are "right" and "left" accoustic channels, i.e., are mirror images of one another. The transducers 2 and 3 are composed of crystalline substrate which vibrate when modulated, i.e., composed of dense, magnetically inert substance. The panel 1 itself may be composed of any magnetically inert medium, such as non-ferrous materials e.g., aluminum, brass, bronze, wood, plastics, plexiglass, etc. Preferably, the panel is composed of lucite.

The high frequency transducer 2 has a lower sound pressure level, while the low frequency transducers 3 has a higher sound pressure level. These transducers 2 and 3 are both piezoelectric speakers. In particular, types of piezoelectric transducers which are suitable for use of the present invention can be found in the following U.S. Pat. Nos.: 3,548,116; 3,786,202; 3,852,529; 3,629,625; 3,676,722; and 4,078,160.

Figure 6:
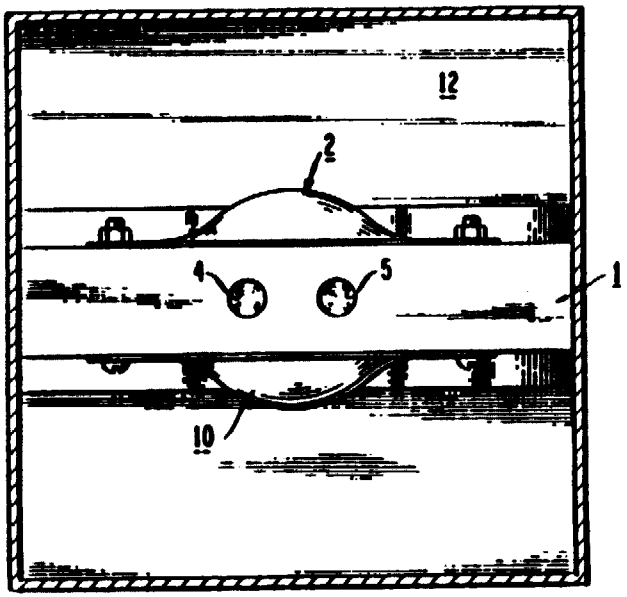
FIG. 6 is a top view a shielded enclosure in which the panel of FIG. 1 is situated.

Two holes 6 and 7 are also provided in the panel 1 for communicating, at one end thereof with the respective bore 5, as illustrated, e.g., in FIGS. 2 and 6. One of these holes 6 is positioned in the panel 1 to open, at an opposite end thereof, adjacent the high frequency transducer 2 when the high frequency transducer 2 is mounted upon the panel 1, while the other hole 7 is positioned in the panel 1 to open at an end opposite the bore or channel 5, adjacent the low frequency transducer 3. The hole 6 is generally larger than the hole 7. For example, hole 6 can have a diameter of about 5/32 inches, while hole 7 has a diameter of about 7/64 inches. Channels 4 and 5 themselves have diameters of about 5/16 inches. These holes and bores or channels can be provided within the panel 1, by conventional drilling, while the transducers 2 and 3, may be conveniently mounted upon the panel 1, by inserting bolts into respective openings provided for the same, as clearly illustrated in the various figures.

A second pair of transducers, namely piezoelectric transducers 10,11 may be provided on a reverse side of the panel 1 as also illustrated, with appropriate holes 8 and 9 being provided in the panel 1 to communicate at ends thereof with the bore or channel 4, and to open at opposite ends thereof adjacent the respective high frequency transducer 10 and low frequency transducer 11. These holes 8, 9 and transducers 10, 11 are analogous to the holes 6,7 and transducers 2,3 described above. Therefore, "right" and "left" sound channels are provided in the system of the invention herein, for stereo reception. The panel 1 itself is about $\frac{3}{4}$ inches thick and has a height of about $3\frac{7}{8}$ inches and a width of about $5\frac{3}{4}$ inches.

Preferably, a membrane is inserted between the respective transducer 2, 3, 10, 11 and the panel itself over the respective hole 6, 7, 8, 9, to block entry of oxygen or air into the transducer, when the acoustic system of the invention is also used in oxygen rooms to provide sound for patients.

The panel 1 is mounted in a box 12 or enclosure which is preferably constructed of copper and is sealed tight, while the other outer room housing the MRI device is also shielded in copper (there is a penetration panel *56* at one point for various circuitry to the MRI device, and also to the acoustic system of the present invention, as explained further below).

The room *50* in which the MRI device and acoustic system is housed, is lined with the copper to eliminate interference from radio frequencies.

Any stray rf interference will be trapped in the enclosure or box 12, because the box or enclosure 12 is rf tight. The enclosure 12 is also grounded at contact 17. A twin-axial cable *54* is attached to the contact 17 which serves to ground box 12 to the penetration panel *56*. Thus, rf shielding is quite clearly accomplished by the invention herein. Furthermore, a sealed wooden box filled with foam may enclose the copper box 12 to attenuate ambient noise created by MRI scanning.

Figure 7:
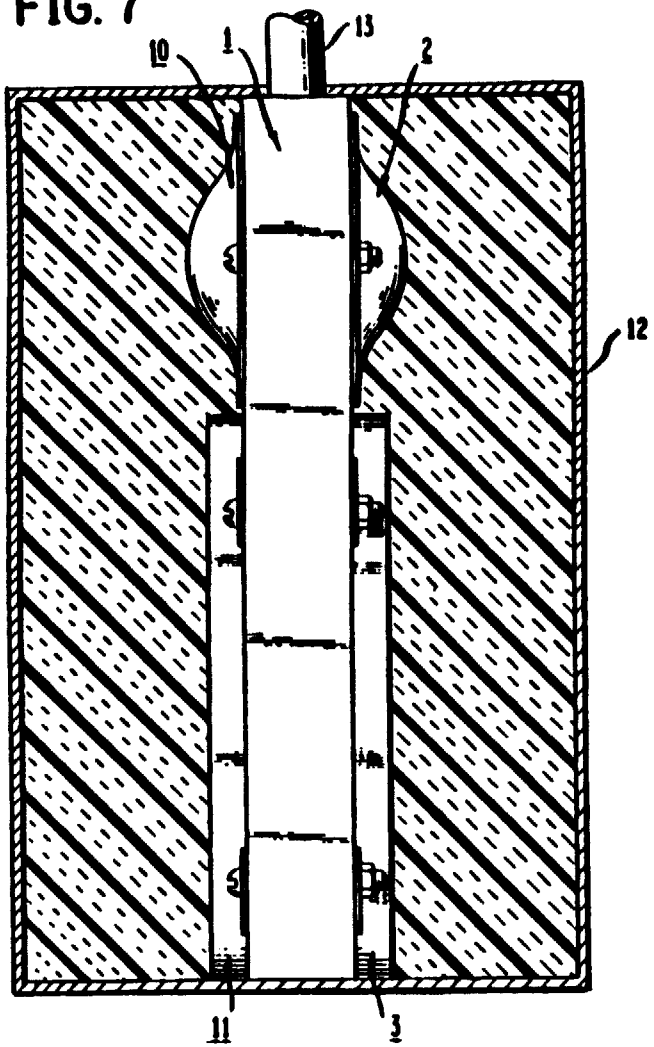
FIG. 7 is a side view of the enclosure of FIG. 6, additionally illustrating insulation therein.
Figure 8:
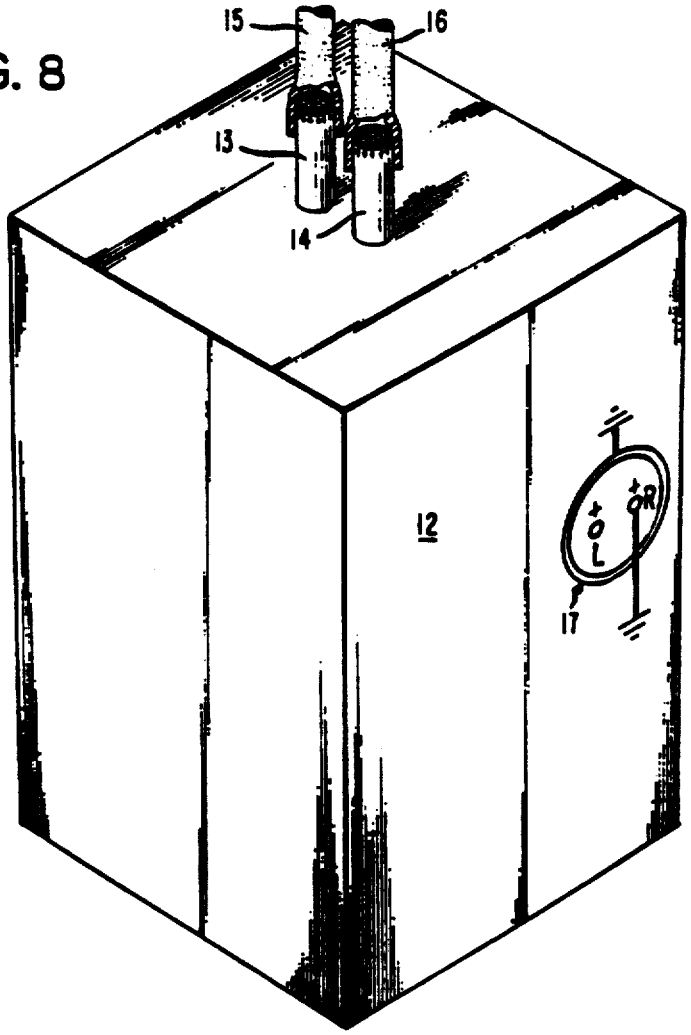
FIG. 8 is a partial perspective view of the enclosure of the FIGS. 6 and 7.

The panel 1 of the present invention is arranged to be mounted within an rf-shielded box 12 as illustrated in FIGS. 6–8. The box 12, as noted above is also constructed of magnetically inert substance. The top of the box or enclosure 12 is provided with two openings in which wave guide tubes 13, 14 are inserted to extend both into and out of the box or enclosure 12, as illustrated in FIG. 8. These tubes 13, 14 communicate with the respective channels 4 and 5 of the panel 1, to be explained further below.

Figure 9:
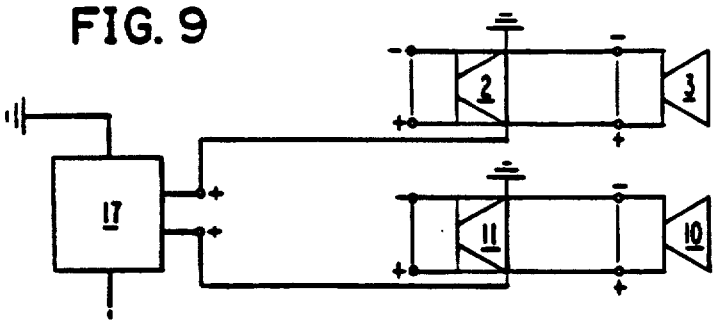
FIG. 9 is a schematic illustration of circuitry applied in accordance with the present invention; [and]
Figure 10:
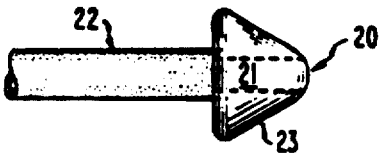
FIG. 10 is a view of an ear piece utilized in accordance with the present invention; *and*

The hookup of the various transducers to the electronic circuit is schematically illustrated in FIG. 9. Basically, lines from the ground 17 are connected to the high frequency transducer 2 and also to the low frequency transducer 11 as illustrated, with the low frequency transducer 3 being appropriately coupled to the high frequency transducer 2, and the high frequency transducer 10, being appropriately coupled to the low frequency transducer 11, as illustrated in FIG. 9. Thus, the circuitry is completed so that electronic energy imparted to the respective transducers, will cause the same to vibrate, in turn pneumatically creating sound in the respective holes 6, 7, 8, 9, which is then transferred through the bores 4 and 5 and along tubing to the respective headset of a patient.

Therefore, the lucite/NMM panel 1 of the present invention incorporates a sound mixing network which permits a flat response. This flat response is achieved the by mixing of the high and low frequencies of the respective transducers. Metering is achieved by differences in the diameter of the sound channels, i.e., the holes from the respective transducers to the main channel bores as described above. More specifically, the flat response of the metering circuit is accomplished by the following:

(1) Variation between the high frequency and low frequency transducers; and (2) Mixing of the high and low frequencies signals in the ported cavity, after the sound is metered, i.e., as the sound leaving the transducers.

Additionally, fine copper mesh screening is soldered to the outlet ports of the wave guide tubes 13 and 14 to further shield from RFI, with suitable pneumatic tubing 15 and 16 being coupled thereabout, as schematically illustrated in FIG. 8. Placement of the copper screening or tobacco mesh further blocks out unwanted rf-waves.

In the acoustic system, a low frequency is generally of the order of about 100–5000 Hz, while a high frequency is generally of the order of about 5000–20,000 Hz.

The sound is transferred pneumatically from the vibrating transducers to the appropriate headset, e.g., based on the bernoulli principle. Any conventional headset may be coupled to the acoustic system in the present invention, e.g., a headset disclosed in U.S. Pat. No. 4,347,911. In this regard, another feature of the present invention is a particular earpiece which can be utilized in the headset incorporated to the acoustic system herein, e.g. the headset disclosed in U.S. Pat. No. 4,347,911.

Figure 11:
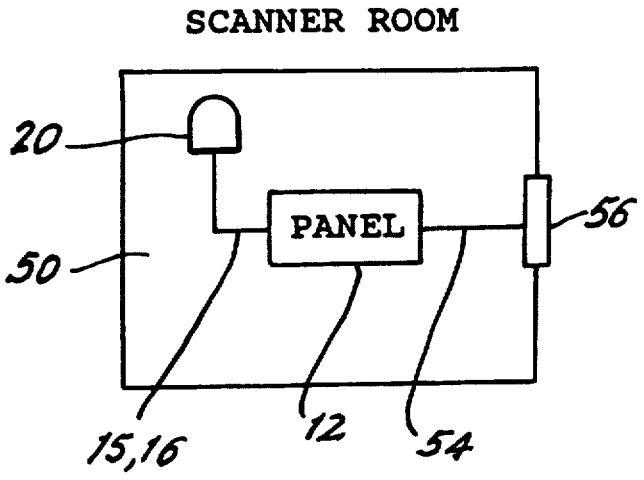
*FIG. 11 is a layout schematic of the sound system of the invention.*

Such an earpiece is illustrated in FIG. 11 of the present case. Basically, this earpiece 20 is constructed of closed-cell foam, is in a conical shape 23, and has a passage for sound 22, 21 extending therethrough to substantially an apex of the conical shape as illustrated. Such an earpiece 20 greatly enhances noise attenuation when utilized along with the other features of the invention herein, as described above.

The preceding description of the present invention is merely exemplary, and is not intended to limit the scope thereof in any way.

What is claimed is:

1. A sound system constructed entirely of magnetically inert *rf-shielded* components which remain unaffected by magnetic fields and do not affect imaging quality, said system comprising a magnetically inert panel, at least one pair of magnetically-inert transducers mounted upon said panel one of which is a high-frequency transducer and the other of which is a low frequency transducer, at least one hollow channel extending into said panel from an edge thereof,

[an rf-tight enclosure, means to mount said panel in said rf-tight enclosure, said rf-tight enclosure comprising an opening to allow a wave guide tube to pass therethrough and communicate with said channel,]

said panel comprising at least one pair of holes, the holes positioned to communicate with said channel at one end thereof and to open said channel at an opposite end thereof adjacent said high frequency or low frequency transducer.

2. The [combination] *system* of claim 1, comprising a pair of hollow channels extending into said panel,

*said at least one pair of transducers comprising* a pair of high frequency transducers and a pair of low frequency transducers mounted upon said panel,

*said at least one pair of holes comprising* two pairs of holes positioned in said panel, with a hole of each said pair positioned in said panel to communicate at one end thereof with one of said channels, and at an opposite end thereof, to open a respective channel adjacent a respective high frequency or low frequency transducer.

3. The [combination] *system* of claim 2, [wherein] *further comprising an rf-tight enclosure, and* said rf-tight enclosure [comprises] *comprising* a pair of openings to allow wave guide tubes to pass therethrough and to communicate with said channels.

4. [The combination of claim 1, additionally comprising] *A sound system constructed entirely of magnetically inert rf-shielded components which remain unaffected by magnetic fields and do not affect imaging quality,*

*said system comprising a magnetically inert panel,*

*at least one magnetically-inert transducer mounted upon said panel,*

*at least one hollow channel extending into said panel from an edge thereof,*

*an rf-tight enclosure in which said panel is mounted,*

*said rf-tight enclosure comprising at least one opening which is effective for enabling a wave guide tube to pass therethrough and communicate with said channel, and* wave guide tubing made of an electrically conductive non-ferrous material mounted in said opening and extending into and out of said enclosure.

5. The combination of claim 3, [additionally] comprising a pair of wave guide tubes, each said tube mounted in a respective [opening] *one of said openings* of said enclosure and extending into and out of said enclosure.

*6. A sound system constructed entirely of magnetically inert components which remain unaffected by magnetic fields and do not affect imaging quality,*

*said system comprising a magnetically inert panel,*

*at least one magnetically-inert transducer mounted upon said panel,*

*at least one hollow channel extending into said panel from an edge thereof,*

*a hole positioned in said panel to communicate at one end thereof with said channel and at an opposite end thereof to open adjacent said at least one transducer,*

*a penetration panel located at a first room in which the magnetically inert panel and an MRI scanner are located; and*

*an electrical cable leading from the penetration panel to the magnetically inert panel.*

*7. The system of claim 1, further comprising a penetration panel at a first room in which the magnetically inert panel and an MRI scanner are located; and*

*an electrical cable leading from the penetration panel to the magnetically inert panel.*

*8. The system of claim 4, further comprising a penetration panel at a first room in which the magnetically inert panel and an MRI scanner are located; and*

*an electrical cable leading from the penetration panel to the magnetically inert panel.*

*9. The system of claim 6, further comprising:*

*acoustic headset means for communicating sound into the ears of a patient; and*

*pneumatic tubing disposed between and connecting the acoustic headset means and the magnetically inert panel.*

*10. The system of claim 7, further comprising:*

*acoustic headset means for communicating sound into the ears of a patient; and*

*pneumatic tubing disposed between and connecting the acoustic headset means and the magnetically inert panel.*

*11. The system of claim 8, further comprising:*

*acoustic headset means for communicating sound into the ears of a patient; and*

*pneumatic tubing disposed between and connecting the acoustic headset means and the magnetically inert panel.*

*12. The system of claim 9, wherein the pneumatic tubing is shorter than 25 feet.*

*13. The system of claim 10, wherein the pneumatic tubing is shorter than 25 feet.*

*14. The system of claim 11, wherein the pneumatic tubing is shorter than 25 feet.*

* * * * *